United States Patent
Denk et al.

(10) Patent No.: US 7,396,949 B2
(45) Date of Patent: Jul. 8, 2008

(54) CLASS OF VOLATILE COMPOUNDS FOR THE DEPOSITION OF THIN FILMS OF METALS AND METAL COMPOUNDS

(76) Inventors: Michael K. Denk, 2456 Mainroyal Street, Mississauga, Ontario (CA) L5L 1C6; Sebastien Fournier, c/o Department of Chemistry University of Toronto, 80 St. George Street, Toronto, Ontario (CA) M5S 3H6

( * ) Notice: Subject to any disclaimer, the term of this patent is extended or adjusted under 35 U.S.C. 154(b) by 597 days.

(21) Appl. No.: 10/643,090

(22) Filed: Aug. 19, 2003

(65) Prior Publication Data
US 2005/0042372 A1 Feb. 24, 2005

(51) Int. Cl.
*C07F 1/00* (2006.01)
(52) U.S. Cl. .................................................. 556/110
(58) Field of Classification Search ............... 556/110
See application file for complete search history.

(56) References Cited

U.S. PATENT DOCUMENTS

| 5,453,494 | A | 9/1995 | Kirlin et al. | |
|---|---|---|---|---|
| 5,834,058 | A | 11/1998 | Wallbridge et al. | |
| 5,840,897 | A | 11/1998 | Kirlin et al. | |
| 6,126,996 | A | 10/2000 | Kirlin et al. | |
| 7,166,732 | B2 * | 1/2007 | Xu et al. | 556/110 |
| 7,241,912 | B2 * | 7/2007 | Xu et al. | 556/110 |

OTHER PUBLICATIONS

Archibald et al., Inorganic Chemistry, vol. 38, No. 24, pp. 5571-5578 (1999).*
Shibayama et al., Macromolecules, vol. 30, No. 11, pp. 3159-3163 (1997).*
Dehnicke et al., Journal of Organometallic Chemistry, vol. 352, No. 1-2, pp. C1-C4 (1988).*
Van Vliet et al., Jornal of organometallic Chemsitry, vol. 179, pp. 89-100 (1979).*
Lim et al., Inorganic Chemistry, vol. 42, No. 24, pp. 7951-7958 (Published on Web Oct. 25, 2003).*
Li et al., Inorganic Chemistry, vol. 44, No. 6, pp. 1728-1735 (Published on Web Feb. 3, 2005).*

* cited by examiner

*Primary Examiner*—Porfirio Nazario Gonzale
(74) *Attorney, Agent, or Firm*—Roylance, Abrams, Berdo & Goodman, L.L.P.

(57) ABSTRACT

The invention provides an organometallic complex, containing oxygen free organic ligands, for the deposition of a metal, preferably copper, silver or gold, and preferably by way of chemical vapor deposition. The organometallic complex having the formula $$[(D_o)_n ML_x]_k$$

where M is a metal preferably selected from the group consisting of Cu, Ag and Au;

$D_o$ is selected from the group comprising ethers, phosphines, olefins, sulfides, pyridines, carbonyl, hydroxyl, cyclopentadiene, benzene derivatives, allyls, alkyls, amines, polyamines, aniline derivatives, cyclooctadiene and combinations thereof;

n is an integer having a value from 0 to 4;
k is an integer having a value from 1 to 4;
x is an integer having a value from 1 to 4; and
L is an amidinate ligand of the formula $$R^1-N=C(R^2)-N-R^3$$

where $R^1$, $R^2$ and $R^3$ are selected from the group consisting of alkyls, allyls, aryls, heteroaryls, hydrogen, non-metals and metalloids; and where $R^1$, $R^2$ and $R^3$ are different or the same.

4 Claims, 6 Drawing Sheets

ORTEP diagram of $\{Cu[^tBuNC(H)N^tBu]\}_2$

Figure 1. ORTEP diagram f of [tBuHNC(H)NHtBu]+ AcO−
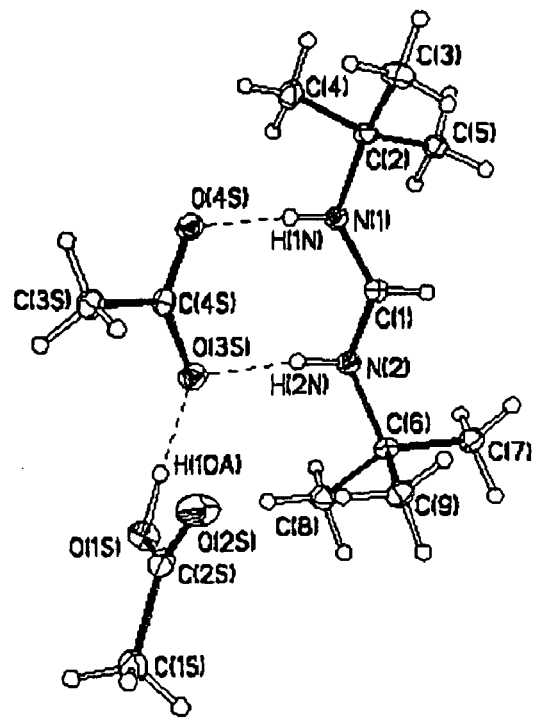
Figure 2. ORTEP diagram of [iPrHNC(H)NHiPr]+ AcO−
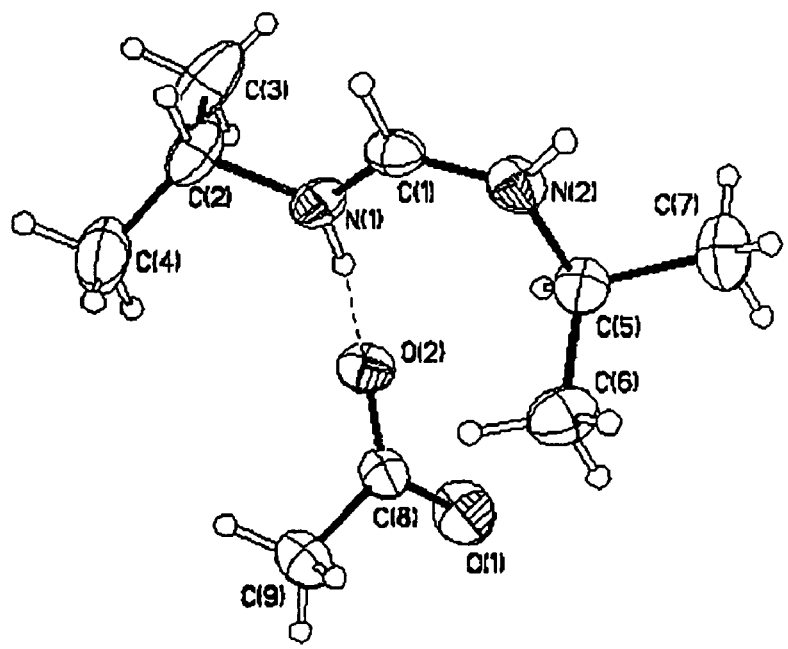

Figur 3. ORTEP diagram of {Cu[tBuNC(H)NtBu]}2
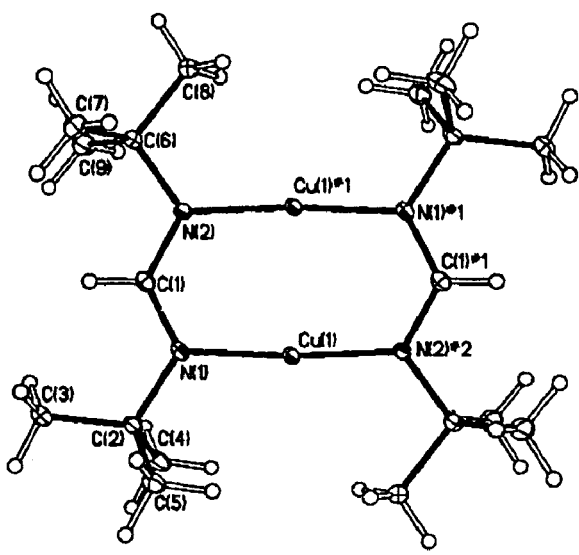
Figure 4. ORTEP diagram of {Ag[tBuNC(H)NtBu]}2
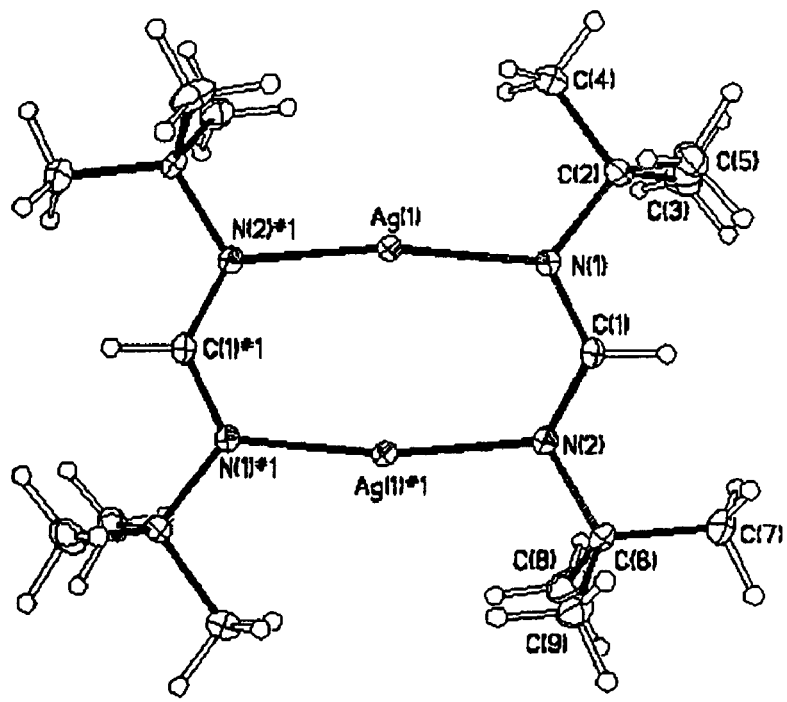

Figure 5. ORTEP diagram of {Au[tBuNC(H)NtBu]}2
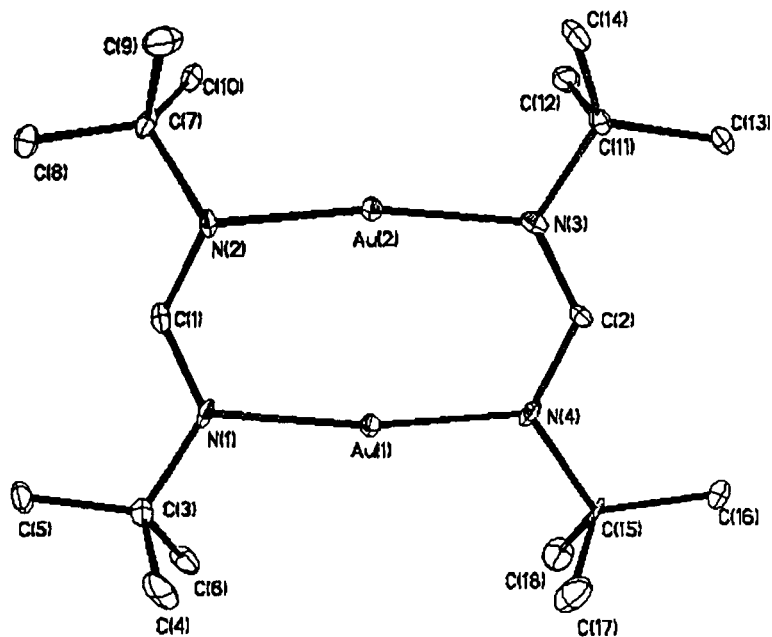
Figure 6. ORTEP diagram of {Cu[iPrNC(H)NiPr]}2
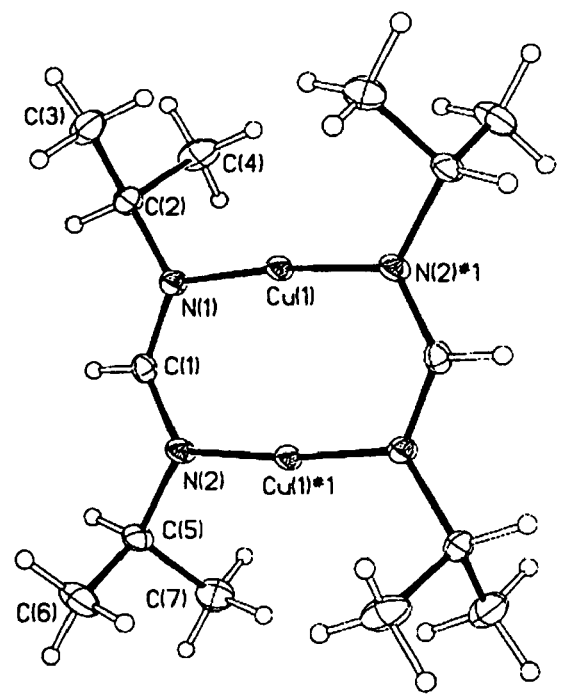

Figure 7a. Picture of the CVD reactor used
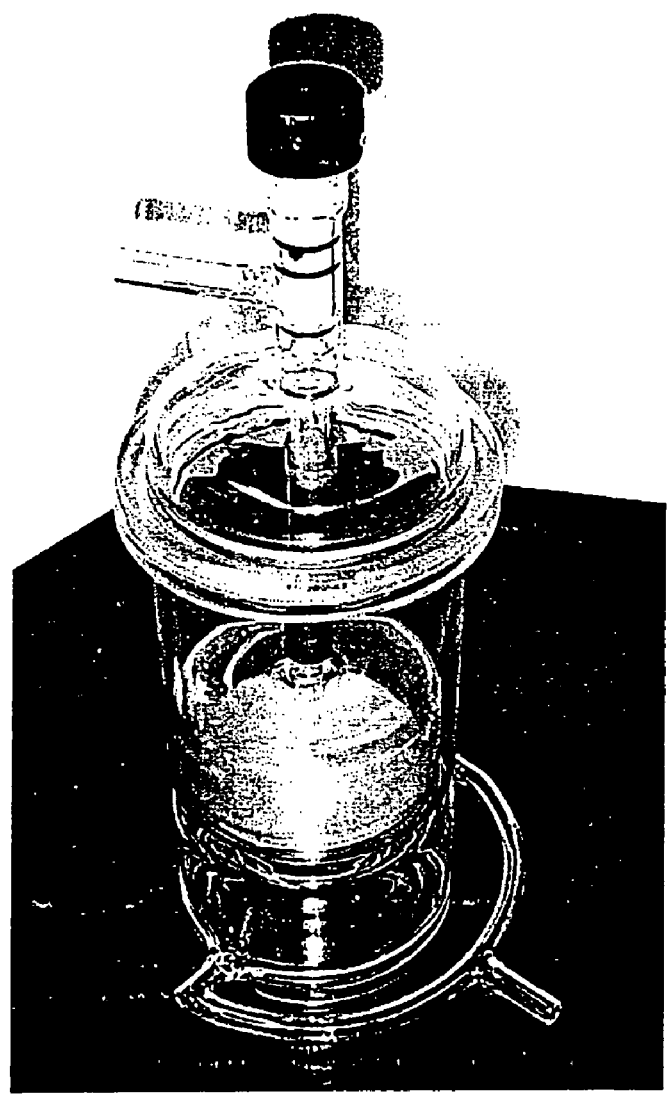

Figure 7b. PXRD spectrum of a copper film obtained by CVD
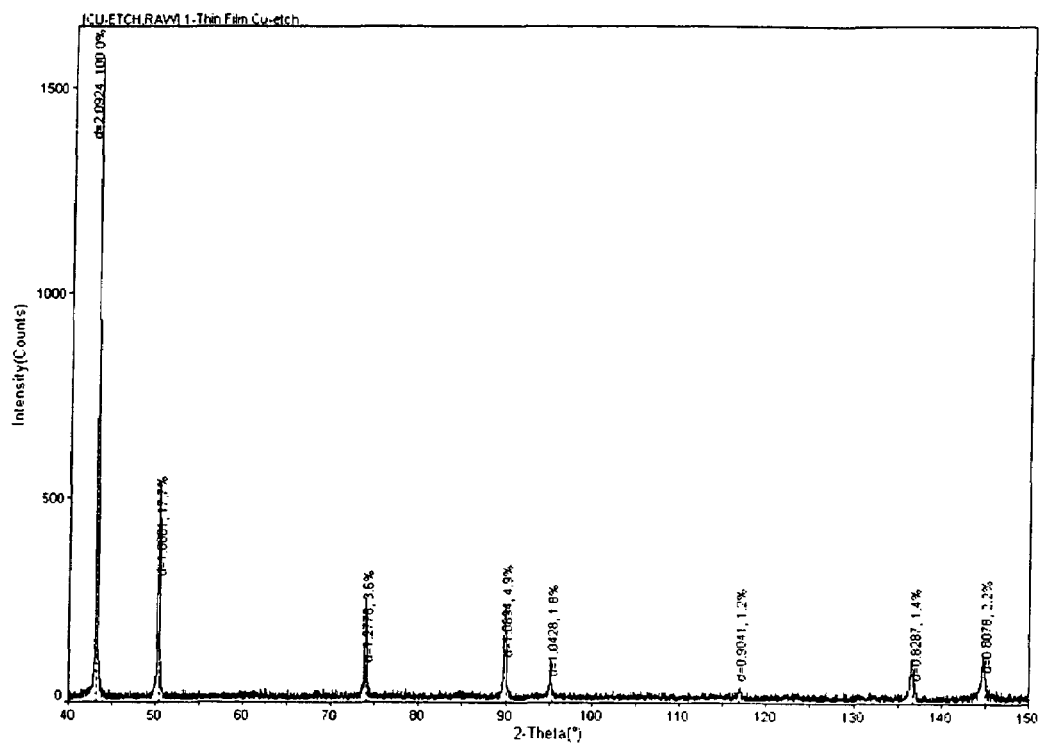

Figure 7c. SEM view of a copper film obtained by CVD
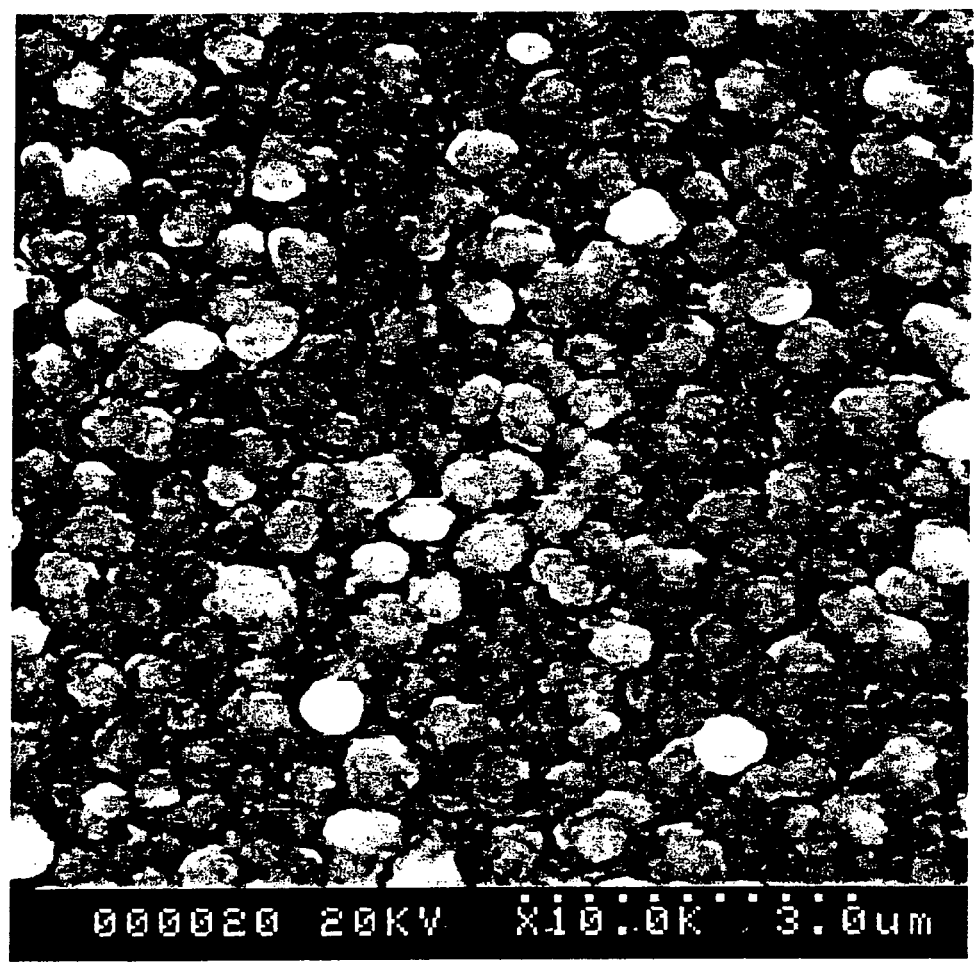

CLASS OF VOLATILE COMPOUNDS FOR THE DEPOSITION OF THIN FILMS OF METALS AND METAL COMPOUNDS

FIELD OF THE INVENTION

The present invention relates to the deposition of thin films of metals and metal compounds and more particularly to the use of oxygen free organometallic complexes for the deposition of copper, silver and gold.

BACKGROUND OF THE INVENTION

The deposition of thin films of pure metals, alloys and semiconductors is of central importance for the manufacturing of microelectronic devices. The materials are generally deposited by the thermal decomposition of volatile compounds (Chemical Vapor Deposition, CVD).

The chemical vapor deposition (CVD) of copper (Cu), silver (Ag), and gold (Au), commonly referred to as the coinage metals, has attracted substantial attention over the last decade. Apart from specialized, small scale applications like the design and repair of X-ray lithographic masks and the generation of monodisperse nanoclusters, the metals have also been attracting attention for use in the manufacturing of microelectronic devices. A fundamental problem resulting from the use of metals is their ohmic resistivity and the heat thus generated. The dissipation of the resistively generated heat has become a limiting factor for microcircuit manufacturing and has led to the replacement of the previously popular aluminum with copper.

CVD of the coinage metals is described in Nast R. et al. *Chem. Ber.* 1963, 96, 2127 and in Nast R. and Lepel, W. H., *Chem. Ber.* 1969, 102, 3224. Although the resulting complexes of the process described are too labile to act as good CVD precursors and are non-volatile due to their polymeric nature, they can be transformed into a new class of volatile Cu(I) complexes by reacting them with donor ligands.

Cu(II) complexes are suitable in the presence of reducing gases, most commonly hydrogen ($H_2$) and the first copper CVD publication reported by van Hermert et al. *J. Electrochem. Soc.* 1965, 112, 1123 was based on this principle.

To this day, the deposition of copper, silver and gold, has almost exclusively relied on the diketonate complexes as described in James, A. M. et al. *Inorg. Chem* 1998, 37, 3785.

The deposition of the coinage metals benefits from the low thermodynamic stability of their respective oxides, carbides, nitrides and hydrides. As a result, reasonably pure metallic films of copper, silver and gold have been obtained from oxygen containing complexes as described, for example, in Nast et al. 1963; Nast et al. 1969; Lakshmanan, Sik and Gil, W. N., *Thin Solid Films* 1999, 338, 24; Edwards D. A., et al. *Mater. Chem.* 1999, 9, 1771; and Holl, M. M. B. et al., *Inorg. Chem.*, 1994, 33, 510. The use of reactive gases, for example $H_2$, and higher substrate temperatures can further reduce contamination with oxygen or carbon, but the presence of oxygen in the ligand is problematic due to the formation of copper oxides which increase the electrical resistance of the copper films because of their semiconductor nature. These same problems apply to other heteroelements like fluorine or phosphorous which are introduced to enhance the volatility of the complexes.

Amidinate complexes of Cu, Ag and Au have been described previously, for example in Kilner M. and Pietryszowski M., *Polyhedron*, 1983, 2, 1379; Cotton, F. A., et al., *J. Am. Chem. Soc.*, 1988, 110, 7077; and Hartmann E. et al., *Naturforsch*, 1989, 44b, 1. However, such complexes are generally non-volatile tetramers of type $Cu_4L_4$ (L=amidine) or dimers that are rendered involatile by the presence of large aryl substituents.

This invention describes the synthesis and use of metal complexes of a specific class of oxygen free organic ligands, known as amidines, to achieve the deposition of a variety of different materials including metals and metal alloys. The deposition reactions are preferably conducted from the gas phase and at elevated temperatures.

Amidinate complexes have been described for a variety of metals but have not been used as precursors for the manufacturing of metals, alloys or metal based materials like metal oxides, metal carbides, etc.

SUMMARY OF THE INVENTION

This invention describes a new class of volatile metal complexes and their use for the deposition of metals, in particular copper, silver and gold.

In one embodiment of the invention the organometallic complex has the formula $$[(D_o)_n ML_x]_k$$

where M is a metal preferably selected from the group consisting of Cu, Ag and Au;

$D_o$ is selected from the group comprising ethers, phosphines, olefins, sulfides, pyridines, carbonyl, hydroxyl, cyclopentadiene, benzene derivatives, allyls, alkyls, amines, polyamines, aniline derivatives, cyclooctadiene and combinations thereof;

n is an integer having a value from 0 to 4;

k is an integer having a value from 1 to 4;

x is an integer having a value from 1 to 4; and

L is an amidinate ligand of the formula

where $R^1$, $R^2$ and $R^3$ are selected from the group consisting of alkyls, allyls, aryls, heteroaryls, hydrogen, non-metals and metalloids; and where $R^1$, $R^2$ and $R^3$ are different or the same.

More preferably the moieties $R^1$ and $R^3$ of the organometallic complex are the same and are either $^tBu$ and $^iPr$. More preferably the ligands (L) of the organometallic complex are N,N'-di-tert-butyl-formamidine or N,N'-di-iso-propyl-formamidine.

In another embodiment, the invention is directed to an organometallic complex of the formula $$H_n ML_x$$

where M is selected from the group consisting of Cu, Ag and Au;

where n and x are integers and $n+x \leq 7$;

where L is an amidinate ligand of the formula

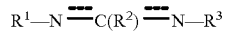

where $R^1$, $R^2$ and $R^3$ are selected from the group consisting of alkyls, allyls, aryls, heteroaryls, hydrogen, non-metals and metalloids excluding trimethylsilyl; and where $R^1$, $R^2$ and $R^3$ are different or the same.

The invention further describes the use of the organometallic complexes for the chemical vapor deposition of a metal, preferably where the metal is one of copper, silver and gold.

BRIEF DESCRIPTION OF THE DRAWINGS

The invention will be better understood with reference to the attached detailed description and to the following drawings, wherein:

FIG. 1 illustrates the molecular structure of [$^tBuHNC(H)NH^tBu$]$^+OAc^-$ in Example 1;

FIG. 2 illustrates the molecular structure of [$^iPrHNC(H)NH^iPr$]$^+OAc^-$ in Example 2;

FIG. 3 illustrates the molecular structure of $\{Cu[^tBuNC(H)N^tBu]\}_2$ in Example 3;

FIG. 4 illustrates the molecular structure of $\{Ag[^tBuNC(H)N^tBu]\}_2$ in Example 4;

FIG. 5 illustrates the molecular structure of $\{Au[^tBuNC(H)N^tBu]\}_2$ in Example 5;

FIG. 6 illustrates the molecular structure of $\{Cu[^iPrNC(H)N^iPr]\}_2$ in Example 6;

FIG. 7a illustrates an embodiment of the reactor used in Example 7;

FIG. 7b illustrates the PXRD spectrum of the copper film of Example 7; and

FIG. 7c illustrates the SEM view of the CVD deposition of copper in Example 7.

DETAILED DESCRIPTION OF THE INVENTION

Amidine complexes described in the literature are typically of general type A or B with metal-metal bonds ranging from non-bonding to quadruple bonds. This combination of 4 amidine ligands with two metals leads to complexes that are typically non-volatile and therefore unsuitable for CVD processes.

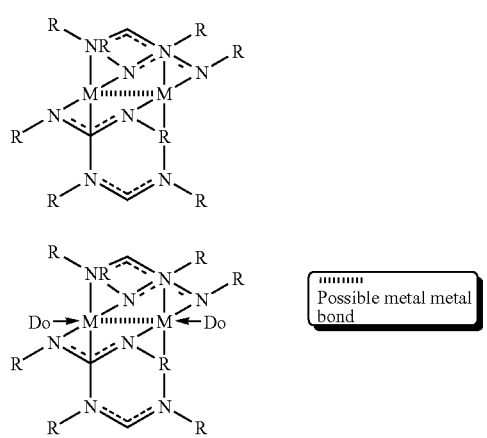

This invention describes volatile complexes of amidines with metals or metalloid elements. These complexes are represented by the general formulas C, D or E.

Although amidines are accessible from inexpensive starting materials, the two preferred amidines of this invention (N,N'-di-tert-butyl-formamidine and N,N'-di-iso-propyl-formamidine) have not previously been reported for use in the synthesis of metal complexes.

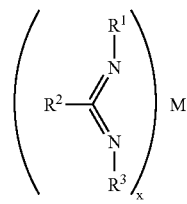

C

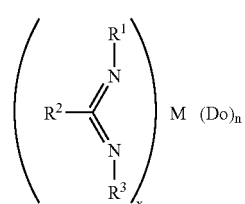

D

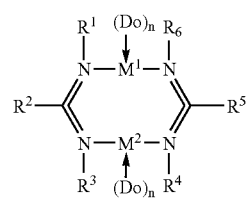

E

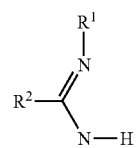

LH

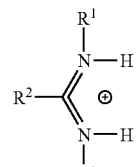

LH$_2$

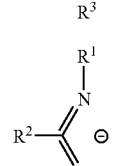

L

For the synthesis of the complexes C-E, the amidines can be used as amidinate anions L combined with monovalent or polyvalent metal cations like Li$^+$, Na$^+$, K$^+$, Mg$^{2+}$, Al$^{3+}$, or as neutral amidines LH, or as amidinium salts containing the cation LH$_2$ in combination with typical monovalent or polyvalent anions X, for example Cl—, Br—, [SO$_4$]$^{2-}$.

The donor ligands D$_o$ may be any suitable donor ligand, which will be known to those skilled in the art, preferably the donor ligands D$_o$ are selected from the group comprising ethers, phosphines, olefins, sulfides, pyridines, carbonyl, hydroxyl, cyclopentadiene, benzene derivatives, allyls, alkyls, amines, polyamines, aniline derivatives, cyclooctadiene and combinations thereof.

For formula D, the index n has a value from n=1 to n=4, most often n=1 or 2, the index x ranges from x=1 to x=5.

For formula E, the index n has a value from n=0 to n=4, most often n=0, 1 or 2.

The precise structure of the complexes can vary from metal to metal and can also be influenced by the nature of the substituents R. For complexes that feature two or more metal atoms in the formula unit, the metals can be either identical or different.

For the use of the complexes it is important that the complexes are either volatile or soluble in common solvents or both.

The combination of the substituents $R^1$ to $R^6$ in formula E is variable. While the combinations $R^1=R^3$ and $R^4=R^6$ have the advantage of relying on the more easily accessible symmetrically substituted amidine ligands or their salts, the synthesis and the use of the compounds are not limited to these combinations.

The substituents R comprise any combination of allyl, alkyl, aryl, heteroaryl, hydrogen nonmetal (e.g. OH, $PR_2$, $NR_2$) or metalloid (e.g. $SiR_3$ or $GeR_3$). Preferably for the deposition of the metals $R^1$, $R^3$, $R^4$ and $R^6$=alkyl or trialkyl silyl and $R^2$, $R^5$=hydrogen with $R^1$, $R^3$, $R^4$ and $R^6$ being all equal, some equal and some different, or all different.

The invention therefore provides an organometallic complex having the formula

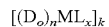

where M is a metal preferably selected from the group consisting of Cu, Ag and Au;

$D_o$ is selected from the group comprising ethers, phosphines, olefins, sulfides, pyridines, carbonyl, hydroxyl, cyclopentadiene, benzene derivatives, allyls, alkyls, amines, polyamines, aniline derivatives, cyclooctadiene and combinations thereof;

n is an integer having a value from 0 to 4;
k is an integer having a value from 1 to 4;
x is an integer having a value from 1 to 4; and
L is an amidinate ligand of the formula

where $R^1$, $R^2$ and $R^3$ are selected from the group consisting of alkyls, allyls, aryls, heteroaryls, hydrogen, non-metals and metalloids; and where $R^1$, $R^2$ and $R^3$ are different or the same.

It will be understood by one of skill in the art, and from the above discussions that the ligand L has a delocalized negative charge.

The invention also comprises the use of the ligands N,N'-di-tert-butyl-formamidine and N,N'-di-iso-propyl-formamidine in the metal complexes used in the deposition of the metals. The invention further comprises an improved synthesis for N,N'-di-tert-butyl-formamidine which is also applicable for the synthesis of the new ligand N,N'-di-iso-propyl-formamidine, an example of the synthesis of the ligands is described in Examples 1 and 2.

The main use of the compounds is in the deposition of metallic coatings in the form of thin or thick films.

The deposition reactions can occur chemically, photochemically, thermally, through the assistance of ultrasound or in other high energy environments exemplified by plasmas, ionizing radiation, visible light, UV light or by chemical vapor deposition coupled with a physical deposition technique.

The depositions can occur from solutions of the complexes in typical organic solvents comprising ethers, hydrocarbons, chlorinated hydrocarbons, nitrites but typically from the gas phase.

The gas phase can consist of pure vapors of the compounds but will typically contain inert gases such as nitrogen, argon or helium, reactive gases like hydrogen or ammonia or mixtures of inert and reactive gases.

The substrates to be coated are typified but not limited to silicon, germanium, gallium arsenide, glass, quartz, steel, plastic as well as hybrid materials consisting of these materials.

The coatings will preferably be the metals or their alloys but can also be nitrides, phosphides, oxides, sulfides, selenides, borides or suicides which are formed if adequate reactive gases like ammonia ($NH_3$), phosphine ($PH_3$), oxygen ($O_2$), hydrogen sulfide ($H_2S$), hydrogen selenide ($H_2Se$), borane ($B_2H_6$) or silane ($SiH_4$) respectively are used.

The deposition of alloys is typically achieved by utilizing solutions or vapors that contain a single complex containing different metal atoms or mixtures of complexes with different metal atoms.

The complexes are obtained from the respective amidines which can be either introduced as salts containing the cations $LH_2$ or the anions L or as neutral amidines LH. In the case of salts, the counterions are typical monovalent, or polyvalent anions comprising chloride, bromide, iodide, tetraphenyborate, carbonate, acetate, sulfate, phosphate or their organic derivatives. For the complexes containing additional donor ligands, the donor ligand Do is introduced during the synthesis.

Due to the difficulties in handling the highly air sensitive neutral amidine LH, the preferred way to achieve the synthesis of the metal complexes uses amidinium salts containing the cations $LH_2$ or the anions L instead of the neutral amidine LH.

The amidinium salts are reacted with typical metal salts $M(X)_n$, where X takes on the same meaning as above and the value n takes on values from 1 to 5. n need not be integral as non-stoichiometric metal salts may also be used.

The reactions are typically carried out in an inert organic solvent (hydrocarbons, ethers) and in the presence of a strong base, typically nBuLi, $NaNH_2$ or NaH to generate the amidine LH or the amidinate L in situ. Heating or cooling can be advantageous to speed up the formation of the complexes. While the presence of a strong base can be advantageous in many cases (higher yield), some metal complexes can also be obtained without additional strong bases.

After evaporation of the solvent, the crude reaction mixtures containing the metal complexes can be used directly for the deposition of the metals but the complexes are typically isolated, by recrystallization, sublimation or chromatographic methods.

FIGS. 3, 4 and 5 show ORTEP diagrams depicting the three-dimensional configuration of the complexes {Cu[$^t$BuNC(H)N$^t$Bu]}$_2$, {Ag[$^t$BuNC(H)NtBu]}$_2$ and {Au[$_t$BuNC(H)N$^t$Bu]}$_2$ respectively. Tables 1-15 are crystallographic data for the complexes of FIGS. 3-5. Tables 1, 6 and 11 show the crystal data and structure refinements; Tables 2, 7 and 12 show the atomic coordinates and equivalent isotropic displacement parameters; Tables 3, 8 and 13 show the bond lengths and angles; Tables 4, 9 and 14 show the anisotropic displacement parameters; and Tables 5, 10 and 15 show hydrogen coordinates and isotropic displacement parameters.

Further details of the preferred embodiments of the present invention will now be illustrated in the following examples that are understood to be non-limiting.

EXAMPLE 1

Synthesis of N,N'-di-tert-butylformamidinium acetate salt

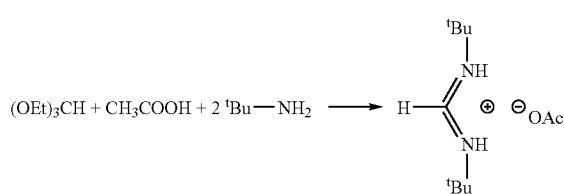

Glacial acetic acid (80.0 mL, 1 equiv. 83.9 g, 1.40 mol) and triethylorthoformate (232 mL, 1 equiv. 207 g, 1.40 mol) were boiled under reflux in a 2 L two-necked round bottom flask equipped with reflux condenser, dropping funnel and magnetic stirrer. After heating the mixture to reflux under an atmosphere of argon, tert-butylamine (289 mL, 2 equiv, 2.80 mol) was added dropwise (slow stream of argon) over a period of two hours. The mixture was boiled for 24 h and the unreacted acetic acid removed by distillation. The residue was purified by a solid distillation (84° C./0.1 torr) to give 248 g (82%) of pure N,N'-di-tert-butylformamidinium acetate. m.p. 60-62° C. The above equation 1 illustrates this reaction.

EXAMPLE 2

Synthesis of N,N'-di-iso-propylformamidinium acetate salt

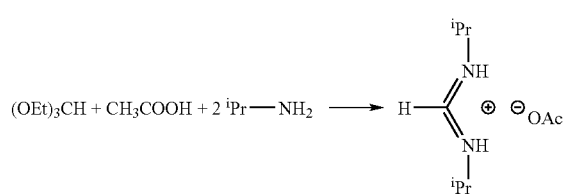

Glacial acetic acid (22.5 mL, 1 equiv.) and triethylorthoformate (59.46 g, 1 equiv.) were introduced into a 250 mL schlenk flask equipped with reflux condenser, dropping funnel and magnetic stirrer. After heating the mixture to reflux under an atmosphere of argon, iso-propylamine (67 mL, 2 equiv.) was added dropwise using the dropping funnel while a slow stream of argon was passed through the condenser. The crude mixture was boiled under reflux for 3.5 d. After removal of the ethanol by distillation, an orange residue was left solidifying partially at room temperature. The formamidinium acetate was isolated by slow sublimation at 40° C./0.1 torr (30% yield), M.p. 83-85° C. The above equation illustrates this reaction.

EXAMPLE 3

Synthesis of Bis[(N,N'-di-tert-butyl-formamidinato) copper(I)]

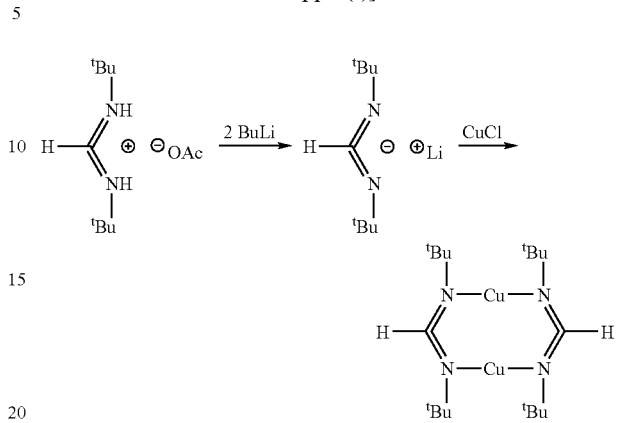

N,N'-di-tert-butyl-formamidinium acetate (7.30 g, 1 equiv.) was introduced into a schlenk flask equipped with a reflux condenser and a cold water bath. n-BuLi (1.6 M solution in hexanes, 42.2 mL, 2 equiv.) was added dropwise and under stirring and the solution boiled for 1 h under reflux. CuCl (3.35 g, 1 equiv.) was added to the cold (r.t.) reaction mixture. After 60 h of stirring at r. t., the solvent was evaporated in vacuo and the remaining solid sublimed at 90° C./0.1 torr. Yield 4.56 g (62%) of colorless crystals. M.p. 230° C. The above equation illustrates this synthesis.

EXAMPLE 4

Synthesis of Bis[(N,N'-di-tert-butyl-formamidinato) silver(I)]

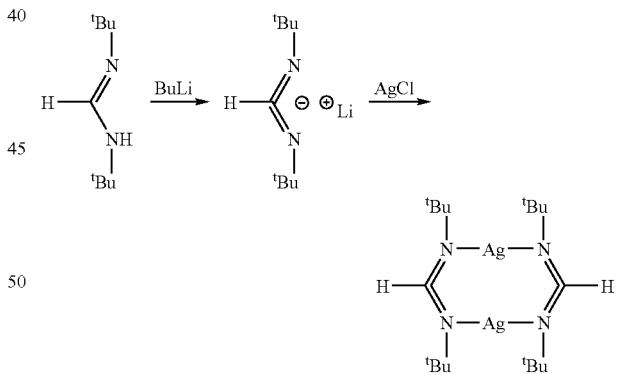

N,N'-di-tert-butyl-formamidine (0.91 g, 1 equiv.) was introduced into a schlenk flask equipped with a reflux condenser and a cold water bath. n-BuLi (1.6 M solution in hexanes, 3.65 mL, 1 equiv.) leading to an exothermic reaction, was added dropwise and the solution was stirred for 3 d. Silver(I) acetate (0.97 g, 1 equiv.) was added under a stream of argon in the reaction flask surrounded with an aluminum foil and the reaction mixture stirred for 4 d. The $^1$H NMR of the brown crude mixture shows only signals for $Ag_2L_2$. After evaporation of the solvent under vacuum, the crude product was purified by sublimation. At 100° C./0.1 torr 0.6 g (40%) of crystalline colorless $Ag_2L_2$ was collected.

EXAMPLE 5

Synthesis of Bis[(N,N'-di-tert-butyl-formamidinato) gold(I)]

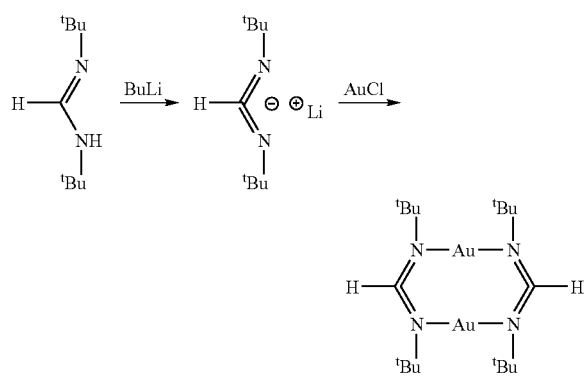

N,N'-di-tert-butyl-formamidine (0.35 g, 1 equiv.) was introduced into a schlenk flask equipped with a reflux condenser and a cold water bath. n-BuLi (1.6 M solution in hexanes, 2.0 mL, 3.1 mmol, 1.4 equiv.) was added dropwise (exothermic reaction) and the solution was stirred for 5 d. AuCl (0.52 g, 1 equiv.) was added along with 10 mL of hexanes under a stream of argon and the reaction mixture stirred for 2 d. The $^1$H NMR of the black crude mixture showed only signals for $Au_2L_2$ in the soluble part. The crude product was purified by frit filtration and 0.47 g (80%) of a light green filtrate was collected.

EXAMPLE 6

Synthesis of Bis[(N,N'-di-iso-propyl-formamidinato) copper(I)]

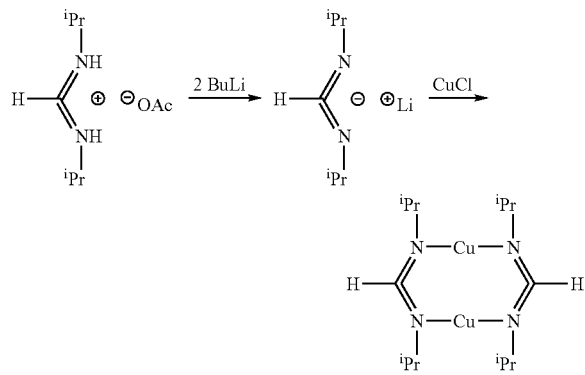

In a Schlenk flask connected to a reflux condenser, N,N'-di-iso-propyl-formamidinium acetate (0.26 g, 1 equiv., 1.4 mmol) was suspended in 10 mL of hexanes. n-BuLi (1.6 M in hexanes, 1.92 mL, 2.2 equiv., 3.1 mmol) was added dropwise and the mixture was refluxed for a few hours until the solution assumed a pale yellow color. CuCl (0.138 g, 1 equiv., 1.4 mmol) was added to the cool reaction mixture and the resulting light green solution was stirred for 6 days at r.t. The hexane soluble fraction was separated from the greenish insoluble fraction by filtration through a medium pore size glass frit. The filtrate was evaporated to dryness under vacuum. Sublimation at 80° C. (0.1 torr) gave 0.28 g (60%) of 6 as colorless solid. M.p. 190-192° C. The above equation illustrates this synthesis.

The complexes obtained in Example 3, 4, 5, 6 and the formamidinium acetate salts of Example 1 and 2 were characterized by single crystal X-ray crystallography, the results of which are seen in FIGS. 1 through 6.

The following example illustrates the process followed for the chemical vapor deposition of copper, however it is understood to be non-limiting and can also be followed for the deposition of silver and gold.

EXAMPLE 7

CVD Deposition Experiments for Copper

To overcome the common problems of obstruction of the delivery pathway by sublimed material resulting from the use of solid, the evaporation vessel was incorporated into the CVD chamber. This eliminated the need to have gradient-heated pipes connecting both. A cold-wall reactor was chosen for the deposition having a vertical design. A medium size glass frit was chosen as support for the precursor and as mixing layer. 0.46 g of copper complex were used in the experiment. The reactor is shown in FIG. 7a.

The reactor contained one central reaction chamber with a removable evaporation vessel (glass frit bottom) supported by a fixed ring on the inside of the reactor wall. The evaporator consisted of a circular glass chamber with a frit at the bottom and a glass tube at the top that served as a gas inlet. The distance between the substrate and the distributor was adjustable by adding glass spacers under the evaporation vessel.

Flow Optimization (Carrier Gas and Vacuum)

The flow of the precursor over the substrate is critical to the formation of high quality films of uniform composition and thickness. Minimization of free convection, recirculation, and buoyancy flows within a reactor are important in the formation of uniform materials. In general, decreasing the pressure of the CVD system simplifies the behavior of the gas flow because high vacuum CVD processes operate under laminar regime and the problems arising from gas flow dynamics are essentially eliminated.

The two parameters used to adjust the flow in this example were the carrier-gas flow rate, and the vacuum (valve between the vacuum pump and the reactor). The temperature in the evaporation vessel was held constant, which ensured that the transport of the precursor was regulated by the flow of the carrier gas. A vacuum of approximately 100 mtorr of hydrogen gas was used.

Temperature Optimization (Substrate and Evaporation Vessel)

To achieve a homogeneous heating of the substrate, ample space to accommodate heating tapes was provided in the form of a cylinder that acted as a support for the substrate. The heating of the evaporation chamber was achieved through a second tape wrapped around the outside of the reactor. Both heating tapes have a heating range of 25 to 480° C. and are controlled using a thermostat.

During deposition experiments, both temperatures were independently controlled and varied in order to obtain an optimum deposition temperature. Fast and homogeneous depositions were obtained when the temperature of the evaporation chamber heating tape was 145° C. and when the temperature of the substrate heating tape was 335° C. Variations in the temperatures of the evaporation chamber heating tape and the substrate heating tape can be made, within the heating range of each of the tapes, for example deposition can also be obtained with the substrate heating tape at 430° C. and the evaporation chamber heating tape at 290° C.

Powder XRD of the copper thin films, shown in FIG. 7b, revealed the presence of pure copper and the absence of crystalline impurities. The thickness of the film was established from an SEM picture, shown in FIG. 7c. The calculated value was 150 nm which provides for a growth rate of ca. 150 Å/min.

While the embodiment discussed herein is directed to a particular implementation of the invention, it will be apparent that variations of this embodiment are within the scope of the invention. For example, the operating parameters, e.g. temperature, flow rates etc. for the CVD experiments can be varied. For example, variations in the substrate heating plate can be made within the range of 335° C. to 430° C. when the evaporation vessel is at 145° C.

We claim:

1. An organometallic complex of the formula $$[(D_o)_N ML_x]_k$$

where M is selected from the group consisting of Cu, Ag and Au;
- $D_o$ is selected from the group consisting of ethers, phosphines, olefins, sulfides, pyridines, carbonyl, hydroxyl, cyclopentadiene, benzene derivatives, allyls, alkyls, amines, polyamines, aniline derivatives, cyclooctadiene and combinations thereof;
- n is an integer having a value from 0 to 4;
- k is an integer having a value from 1 to 4;
- x is an integer having a value from 1 to 4; and
- L is an amidinate ligand of the formula $$R^1\!-\!N\!=\!C(R^2)\!=\!N\!-\!R^3$$

where $R^1$, $R^2$ and $R^3$ are selected from the group consisting of alkyls, allyls, heteroaryls, hydrogen, non-metals and metalloids excluding trimethylsilyl; and where $R^1$, $R^2$ and $R^3$ are different or the same.

2. The organometallic complex of claim 1 wherein $R^1$ and $R^3$ are the same and are selected from the group consisting of $^tBu$ and $^iPr$.

3. An organometallic complex of the formula $$H_n ML_x$$

where M is selected from the group consisting of Cu, Ag and Au;
where n and x are integers and n+x≦7;
where L is an amidinate ligand of the formula $$R^1\!-\!N\!=\!C(R^2)\!=\!N\!-\!R^3$$

where $R^1$, $R^2$ and $R^3$ are selected from the group consisting of alkyls, allyls, aryls, heteroaryls, hydrogen, non-metals and metalloids excluding trimethylsilyl; and where $R^1$, $R^2$ and $R^3$ are different or the same.

4. The organometallic complex of claim 3 wherein $R^1$ and $R^3$ are the same and are selected from the group consisting of $^tBu$ and $^iPr$.

* * * * *